United States Patent
Collins (10) Patent No.: US 6,519,316 B1
(45) Date of Patent: Feb. 11, 2003

(54) INTEGRATED CONTROL OF PORTAL IMAGING DEVICE

(75) Inventor: William F. Collins, Clayton, CA (US)

(73) Assignee: Siemens Medical Solutions USA, Inc.., Malvern, PA (US)

( * ) Notice: Subject to any disclaimer, the term of this patent is extended or adjusted under 35 U.S.C. 154(b) by 0 days.

(21) Appl. No.: 10/053,414

(22) Filed: Nov. 2, 2001

(51) Int. Cl.[7] .................................................. A61N 5/10
(52) U.S. Cl. ......................................................... 378/65
(58) Field of Search ........................................... 378/65

(56) References Cited

U.S. PATENT DOCUMENTS 5,138,647 A * 8/1992 Nguyen ........................ 378/65
6,208,712 B1 * 3/2001 Hernandez-Guerra ........ 378/65

* cited by examiner

Primary Examiner—Craig E. Church (57) ABSTRACT

A system, method, apparatus, and means for controlling a portal imager includes operating a radiation therapy device to identify segment data defining a radiation therapy segment, identifying (from the segment data) portal position information, and positioning a portal imaging device based on the portal position information. The radiation therapy device may be further operated to identify field information identifying a radiation field to be delivered, position elements of the radiation therapy device to deliver the field, deliver the field, and capture a portal image on the portal imaging device.

20 Claims, 5 Drawing Sheets

INTEGRATED CONTROL OF PORTAL IMAGING DEVICE

CROSS-REFERENCE TO RELATED APPLICATIONS

This application is related to commonly owned U.S. patent application Ser. No. 09/909,589, filed Jul. 20, 2001, for "AUTOMATED DELIVERY OF TREATMENT FIELDS" the contents of which is incorporated by reference in its entirety for all purposes.

BACKGROUND OF THE INVENTION

1. Field of the Invention

The present invention relates generally to radiation therapy devices, and more particularly, to the automated delivery and monitoring of radiation therapy.

2. Description of the Related Art

Conventional radiation therapy typically involves directing a radiation beam at a tumor in a patient to deliver a predetermined dose of therapeutic radiation to the tumor according to an established treatment plan. This is typically accomplished using a radiation therapy device such as the device described in U.S. Pat. No. 5,668,847 issued Sep. 16, 1997 to Hernandez, the contents of which are incorporated herein for all purposes.

The radiotherapy treatment of tumors involves three-dimensional treatment volumes which typically include segments of normal, healthy tissue and organs. Healthy tissue and organs are often in the treatment path of the radiation beam. This complicates treatment, because the healthy tissue and organs must be taken into account when delivering a dose of radiation to the tumor. While there is a need to minimize damage to healthy tissue and organs, there is an equally important need to ensure that the tumor receives an adequately high dose of radiation. Cure rates for many tumors are a sensitive function of the dose they receive. Therefore, it is important to closely match the radiation beam's shape and effects with the shape and volume of the tumor being treated. It is also important to properly position the patient on the treatment table to avoid damaging tissue and critical organs.

Portal imaging techniques have been developed to assist in positioning patients, and in verifying the shape of a field delivered to a treatment area on the patient. Most portal imaging techniques utilize photographic films which are carefully positioned by an operator by hand. Because most radiation therapy devices are located within vaults constructed with thick concrete walls and thick doors which can take 30 seconds to open and close, it can take a significant amount of time for an operator to position the film, leave the room, operate the radiation therapy device to deliver radiation, and enter the room to remove the film with the captured portal image.

Electronic portal imaging techniques have also been used which avoid the need to switch films to take multiple images and which eliminates the need to process and expose films to view a portal image. Such electronic techniques, however, still require manual intervention by an operator to configure and manipulate the portal imager, by entering the treatment room. It would be desirable to provide a portal imaging approach which reduces or eliminates the amount of manual intervention required. It would further be desirable to provide a portal imaging approach which integrates control of the portal imager with operation of the radiation therapy device.

SUMMARY OF THE INVENTION

According to one embodiment of the present invention, a system, method, apparatus, and means for controlling a portal imager includes operating a radiation therapy device to identify segment data defining a radiation therapy segment, identifying (from the segment data) portal position information, and positioning a portal imaging device based on the portal position information. The radiation therapy device may be further operated to identify field information identifying a radiation field to be delivered, position elements of the radiation therapy device to deliver the field, deliver the field, and capture a portal image on the portal imaging device.

In some embodiments, the portal imaging device is a flat panel detector movably coupled to a gantry of the radiation therapy device. In some embodiments, the portal imaging device is positioned using a drive motor controlled by control signals received from an operators console. In some embodiments, the portal imaging device may be positioned a number of times during a treatment based on position information for each segment of the treatment.

The present invention is not limited to the disclosed preferred embodiments, however, as those skilled in the art can readily adapt the teachings of the present invention to create other embodiments and applications.

BRIEF DESCRIPTION OF THE DRAWINGS

The exact nature of this invention, as well as its objects and advantages, will become readily apparent from consideration of the following specification as illustrated in the accompanying drawings, in which like reference numerals designate like parts throughout the figures thereof, and wherein.

DETAILED DESCRIPTION

The following description is provided to enable any person skilled in the art to make and use the invention and sets forth the best modes contemplated by the inventor for carrying out the invention. Various modifications, however, will remain readily apparent to those skilled in the art.

Figure 1:
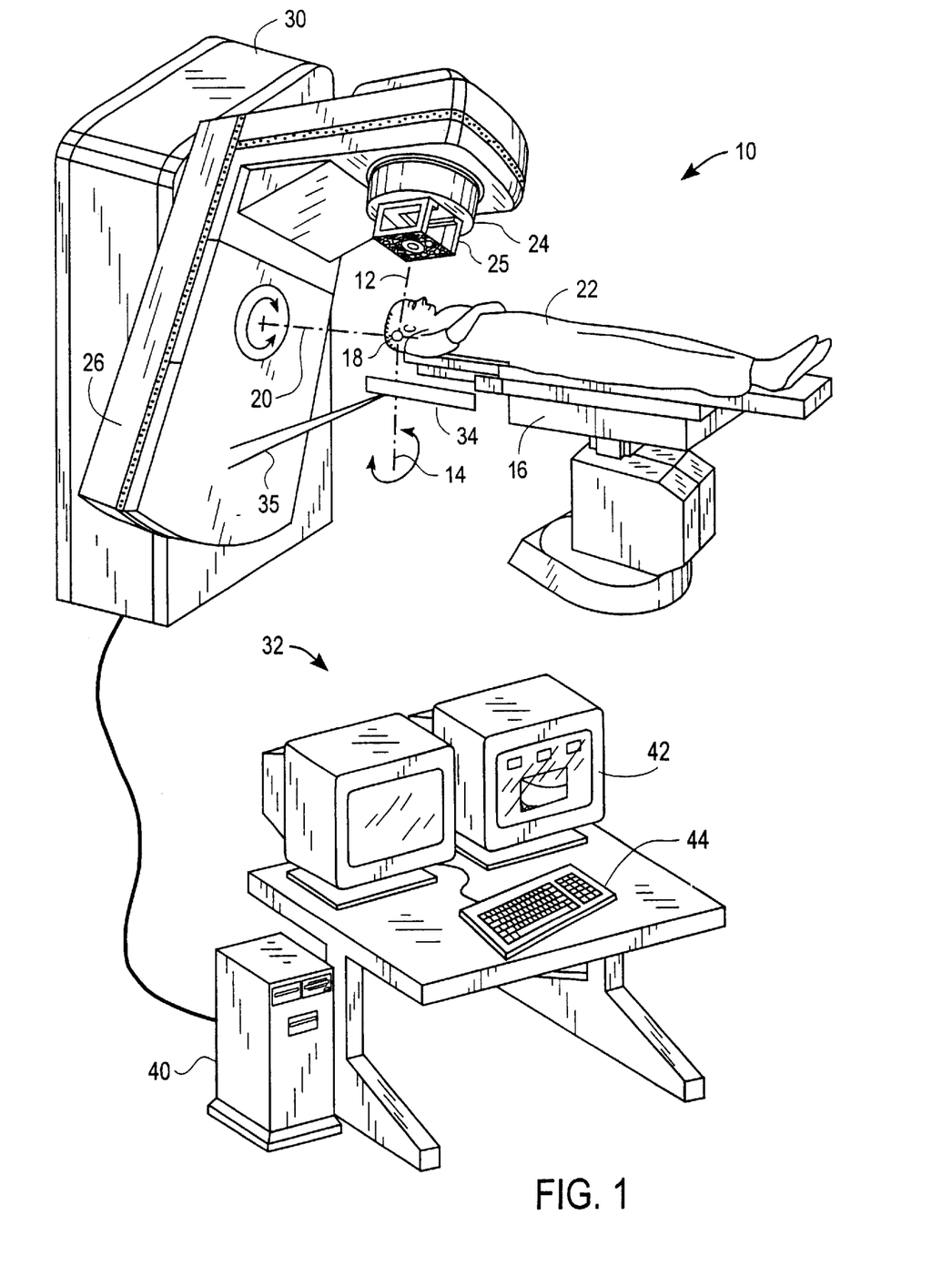
FIG. 1 is diagram illustrating a radiation therapy device including a portal imaging device pursuant to some embodiments of the present invention.

Turning now to the drawings and, with particular attention to FIG. 1, a radiation therapy device 10 pursuant to embodiments of the present invention is shown. According to one embodiment of the present invention, radiation therapy device 10 includes a beam shielding device (not shown) within a treatment head 24, a control unit in a housing 30 and a treatment unit 32. An accessory tray 25 is mounted to an exterior of treatment head 24. Accessory tray 25, in one embodiment, is configured to receive and securely hold attachments used during the course of treatment planning and treatment (such as, for example, reticles, wedges, or the like).

Radiation therapy device 10 includes a gantry 26 which can be swiveled around a horizontal axis of rotation 20 in the course of a therapeutic treatment. Treatment head 24 is fastened to a projection of the gantry 26. A linear accelerator (not shown) is located inside gantry 26 to generate the high energy radiation required for the therapy. The axis of the radiation bundle emitted from the linear accelerator and the gantry 26 is designated by beam path 12. Electron, photon or any other detectable radiation can be used for the therapy.

Radiation therapy device 10 also includes a central treatment processing or control unit 32 which is typically located apart from radiation therapy device 10. Radiation therapy device 10 is normally located in a different room to protect the therapist from radiation. For example, radiation therapy device 10 may be located in a heavily shielded room, such as a concrete vault, which shields the operator from dangerous megavoltage ionizing radiation generated by radiation therapy device 10.

Treatment unit 32 includes a processor 40 in communication with an operator console 42 (including one or more visual display units or monitor) and an input device such as a keyboard 44. Data can be input also through data carriers such as data storage devices or a verification and recording or automatic setup system. More than one control unit 32, processor 40, and/or operator console 42 may be provided to control radiation therapy device 10.

Treatment processing unit 32 is typically operated by a therapist who administers actual delivery of radiation treatment as prescribed by an oncologist. Therapist operates treatment processing unit 32 by using keyboard 44 or other input device. The therapist enters data defining the radiation dose to be delivered to the patient, for example, according to the prescription of the oncologist. The program can also be input via another input device, such as a data storage device. Various data can be displayed before and during the treatment on the screen of operator console 42.

During a course of treatment, the radiation beam is trained on treatment zone 18 of an object 22, for example, a patient who is to be treated and whose tumor lies at the isocenter of the gantry rotation. The plates or leaves of the beam shielding device within the treatment head 24 are substantially impervious to the emitted radiation. The collimator leaves or plates are mounted between the radiation source and the patient in order to delimit (conform) the field. Areas of the body, for example, healthy tissue, are therefore subject to as little radiation as possible and preferably to none at all. The plates or leaves are movable such that the distribution of radiation over the field need not be uniform (one region can be given a higher dose than another). Furthermore, the gantry can be rotated so as to allow different beam angles and radiation distributions without having to move the patient.

According to embodiments of the present invention, radiation therapy device 10 includes an imaging device 34 which is used, as will be described further below, to perform portal imaging for radiation therapy treatments. Imaging device 34 may be attached to gantry 26 via an extendible and retractable arm structure 35. Pursuant to embodiments of the present invention, imaging device 34 may be advanced to, and retracted from, an imaging position along beam path 12.

Control of imaging device 34 is integrated with operation of other components of radiation therapy device 10. For example, data defining a prescribed course of treatment which is stored at, or otherwise accessible to, computer 40, may include data which manipulates elements of radiation therapy device 10 to deliver a prescribed course of radiation and it may also include data which causes imaging device 34 to be extended, retracted, and otherwise manipulated to capture portal images.

Pursuant to embodiments of the present invention, this integrated control allows portal images to be captured without requiring manual intervention by an operator, and further, without requiring the operator to enter the room to manipulate controls of the imaging device. Accuracy and control of treatments and capture of portal images are believed to be improved because the control is integrated with control of other elements of radiation therapy device 10.

Imaging device 34, in one embodiment, is a flat panel imaging device using solid state amorphous silicon sensors. The RID 1640, offered by PerkinElmer®, Inc. of Fremont Calif. is one suitable device. In one embodiment, the imaging device used as imaging device 34 is formed with a plurality of detector elements formed in a two dimensional array. In one embodiment, each detector element (or "pixel") in the array is a solid state sensor, such as a solid state amorphous silicon sensor. Operation of imaging device 34 may result in the capture of a two dimensional image. In one embodiment, computer 40, in conjunction with control electronics which will be described further below, operate to control imaging device 34 to capture an image and map the signal detected by each of the detector elements to a gray scale value, providing a graphical depiction of the captured image.

Imaging device 34 may be attached to gantry 26 via arm structure 35 or in some other manner which allows it to be adjustably placed under patient 22 and along beam path 12. In some embodiments, imaging device 34 has sufficient sensitivity and dynamic range to allow it to take portal images for different types of radiation (e.g., including electron, photon, and mixed beams). In some embodiments, imaging device 34 is used to verify the shape and intensity of fields during the course of a treatment as well as to verify the position of the patient and the field. In some embodiments, imaging device 34 is used to take pre- or post-treatment portal images, in others, it is used to take portal images during treatment. According to some embodiments, imaging information captured by imaging device 34 is transmitted to treatment processing unit 32, allowing the radiation therapist to make any necessary beam or positioning adjustments.

Figure 2:
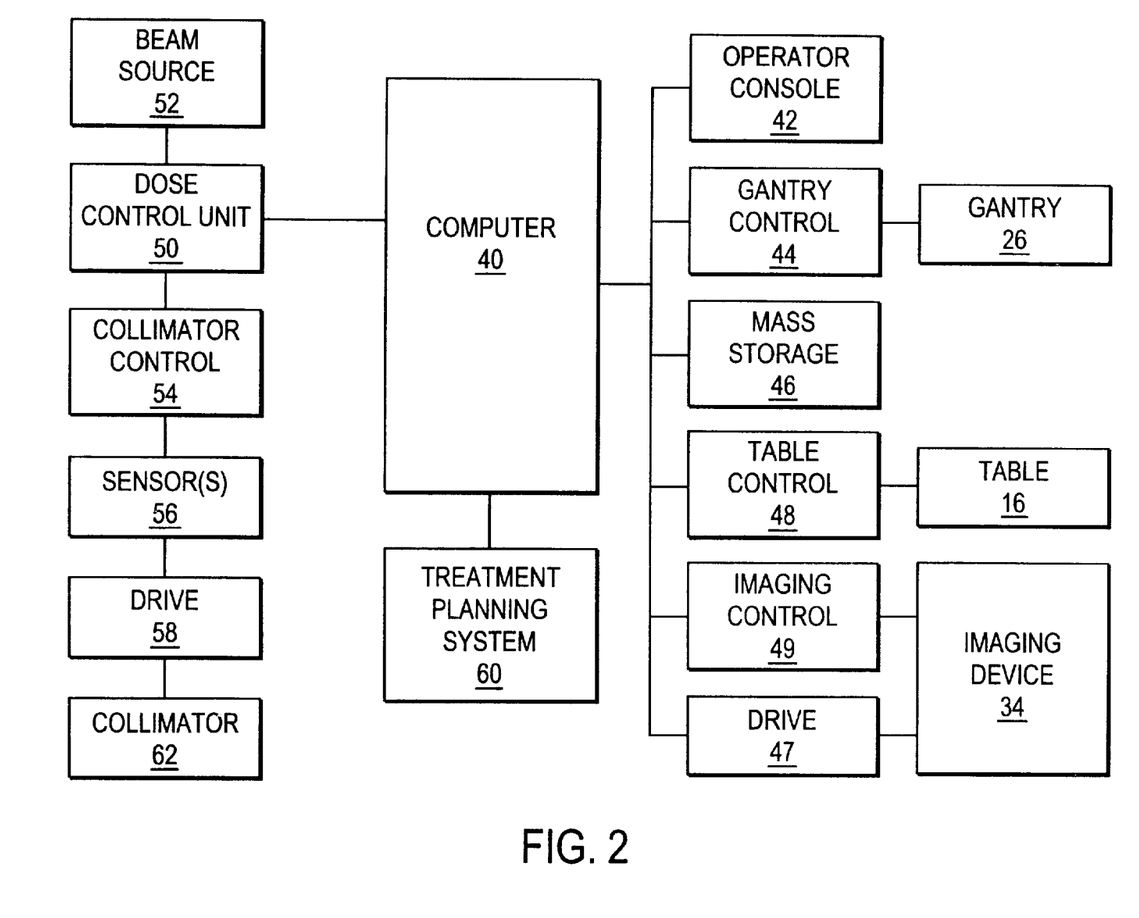
FIG. 2 is a block diagram illustrating portions of the radiation therapy device of FIG. 1 according to some embodiment of the present invention.

Referring now to FIG. 2, a block diagram is shown depicting portions of a radiation therapy device 10 and treatment unit 32 according to one embodiment of the present invention. In particular, treatment delivery elements of a radiation therapy device are shown, which may be configured in radiation therapy device 10 and treatment unit 32 as depicted in FIG. 1. The treatment delivery elements include a computer 40, operatively coupled to an operator console 42 for receiving operator control inputs and for displaying treatment data to an operator.

Operator console 42 is typically operated by a radiation therapist who administers the delivery of a radiation treatment as prescribed by an oncologist. Using operator console 42, the radiation therapist enters data that defines the radiation to be delivered to a patient. The radiation therapist also enters data that defines the capture of portal images during the course of a treatment plan. As used herein, an overall treatment for a patient may be broken into a number of different "segments", each having one or more "port" position of the gantry. The radiation therapist may enter data defining one or more ports at which a portal image is to be taken using imaging device 34. Data defining the different portal images to be taken during a treatment is integrated with other data defining actions to be taken during a particular segment (e.g., such as the radiation to be delivered to the patient and the shape of the field to be used at each port). As a result, control of imaging device 34 is integrated with control of other elements of radiation therapy device 10.

Mass storage device 46 stores data used and generated during the operation of the radiation therapy device including, for example, treatment data as defined by an oncologist for a particular patient. This treatment data is generated, for example, using a treatment planning system 60 which may include manual and computerized inputs to determine a beam shape prior to treatment of a patient. Treatment planning system 60 is typically used to define and simulate a beam shape required to deliver an appropriate therapeutic dose of radiation to treatment zone 18.

Data defining the beam shape and treatment are stored, e.g., in mass storage device 46 for use by computer 40 in delivering treatment. Data defining positioning of imaging device 34 are also stored in, or accessible to, mass storage device 46 for use by computer 40 in delivering treatment. According to some embodiments of the present invention, treatment planning may include activities which occur prior to the delivery of the treatment, such as the generation of treatment data defining a photon treatment, an electron treatment, and/or a mixed beam treatment.

Mass storage device 46 may also store other information and programs used to operate radiation therapy device 10. For example, mass storage device 46 may store one or more interlock libraries, each defining one or more interlocks to be used in the operation of radiation therapy device 10 in a particular operation mode (e.g., different interlocks may be used depending on whether the treatment uses primary electrons, primary photons, or mixture of primary electrons and primary photons). One or more interlock libraries defining permitted positions of imaging device 34 may also be generated (e.g., extension of imaging device 34 may be prevented when the extension would interfere with a particular patient or table position).

Although a single computer 40 is depicted in FIG. 2, those skilled in the art will appreciate that the functions described herein may be accomplished using one or more computing devices operating together or independently. Those skilled in the art will also appreciate that any suitable general purpose or specially programmed computer may be used to achieve the functionality described herein.

Computer 40 is also operatively coupled to various control units including, for example, a gantry control 44 and a table control 48. In operation, computer 40 directs the movement of gantry 26 via gantry control 44 and the movement of table 16 via table control 48. These devices are controlled by computer 40 to place a patient in a proper position to receive treatment from the radiation therapy device. In some embodiments, gantry 26 and/or table 16 may be repositioned during treatment to deliver a prescribed dose of radiation.

According to some embodiments of the present invention, computer 40 is operatively coupled to a imaging device control 49. Imaging device control 49 is used to control the operation of imaging device 34 to perform treatment field verifications and to capture portal images pursuant to embodiments of the present invention. Embodiments of the present invention permit the integrated control and capture of portal images in conjunction with radiation therapy. Imaging device control 49 may also be used to control the positioning of imaging device 34. In some embodiments, gantry control 44 may be used to control the positioning of imaging device 34. In particular, imaging device control 49 (or gantry control 44) may be used to control the operation of imaging device drive 47 which is manipulated to extend and retract imaging device 34 as desired.

According to one embodiment of the present invention, computer 40 and imaging device control 49 perform processing to enhance or manipulate the image captured by imaging device 34 (e.g., as described in the co-pending U.S. Patent Application for "VERIFICATION OF TREATMENT FIELDS" referred to above). As a result, processing performed by computer 40 and imaging device control 49 may be used to generate a portal image depicting the patient anatomy and the photon or electron collimator field edge.

Computer 40 is also operatively coupled to a dose control unit 50 which includes a dosimetry controller and which is designed to control a beam source 52 to generate a desired beam achieving desired isodose curves. Beam source 52 may be one or more of, for example, an electron, and/or photon beam source. Beam source 52 may be used to generate radiation beams in any of a number of ways well-known to those skilled in the art. For example, beam source 52 may include a dose control unit 50 used to control a trigger system generating injector trigger signals fed to an electron gun in a linear accelerator (not shown) to produce en electron beam as output. Beam source 52 is typically used to generate a beam of therapeutic radiation directed along an axis (as shown in FIG. 1 as item 12) toward treatment zone 18 on patient 22.

According to one embodiment of the invention, the beam generated by beam source 52 is shaped using one or more collimators 62. Collimator 62 is manipulated by collimator control 54 utilizing sensor(s) 56 and drive unit 58.

Figure 3:
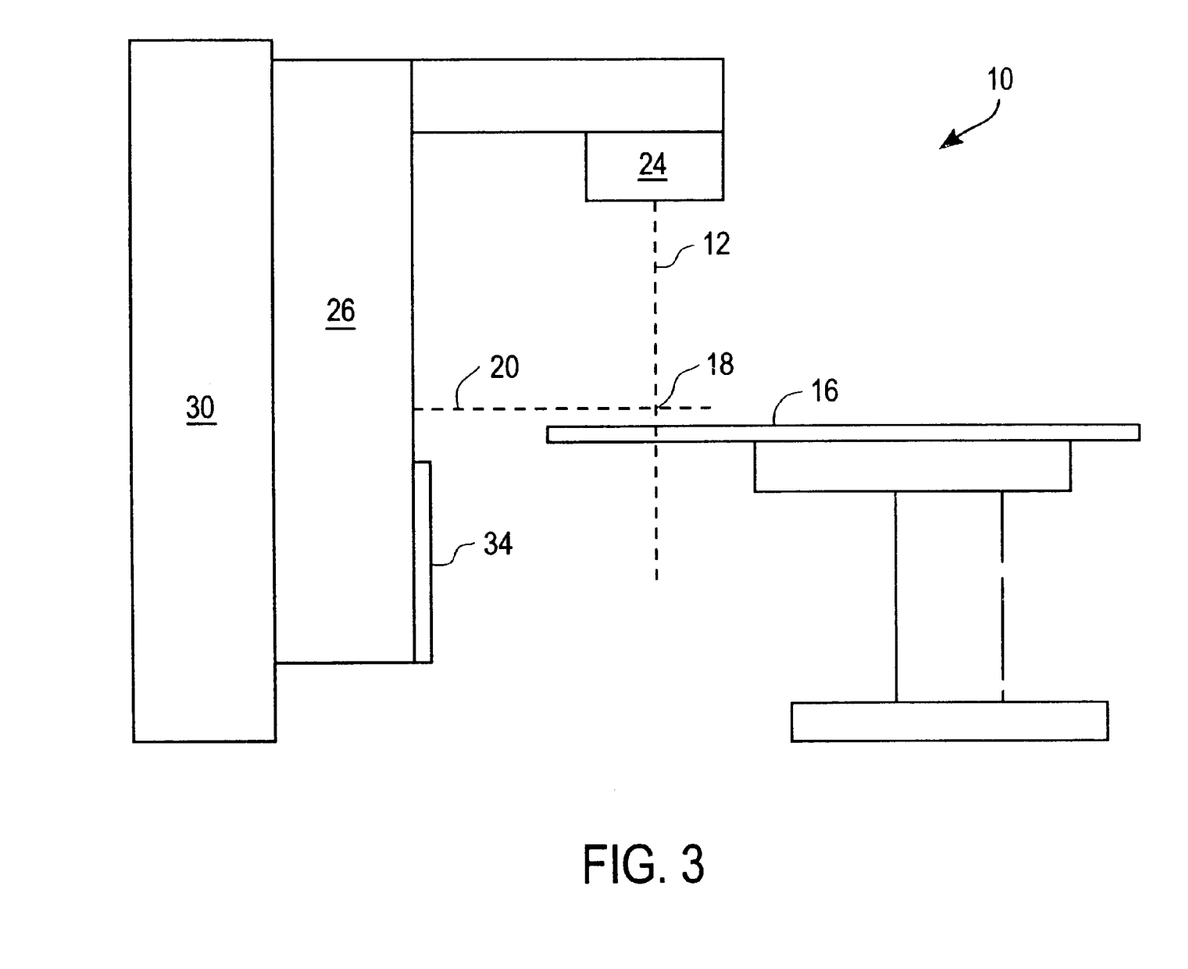
FIG. 3 is a side view of the radiation therapy device of FIG. 1 showing a retracted portal imaging device.

Referring now to FIG. 3, a side view of portions of radiation therapy device 10 is shown. In particular, FIG. 3 depicts a view of radiation therapy device 10 in which imaging device 34 is in a retracted position (e.g., moved out of beam path 12 and secured to a housing of gantry 26). In this position, gantry 26 may be freely rotated about axis 20 to direct a beam of therapeutic radiation along beam axis 12 toward a treatment zone 18 without interference from imaging device 34. Further, in this retracted position, sensitive electronics within imaging device 34 may be protected from irradiation.

Figure 4:
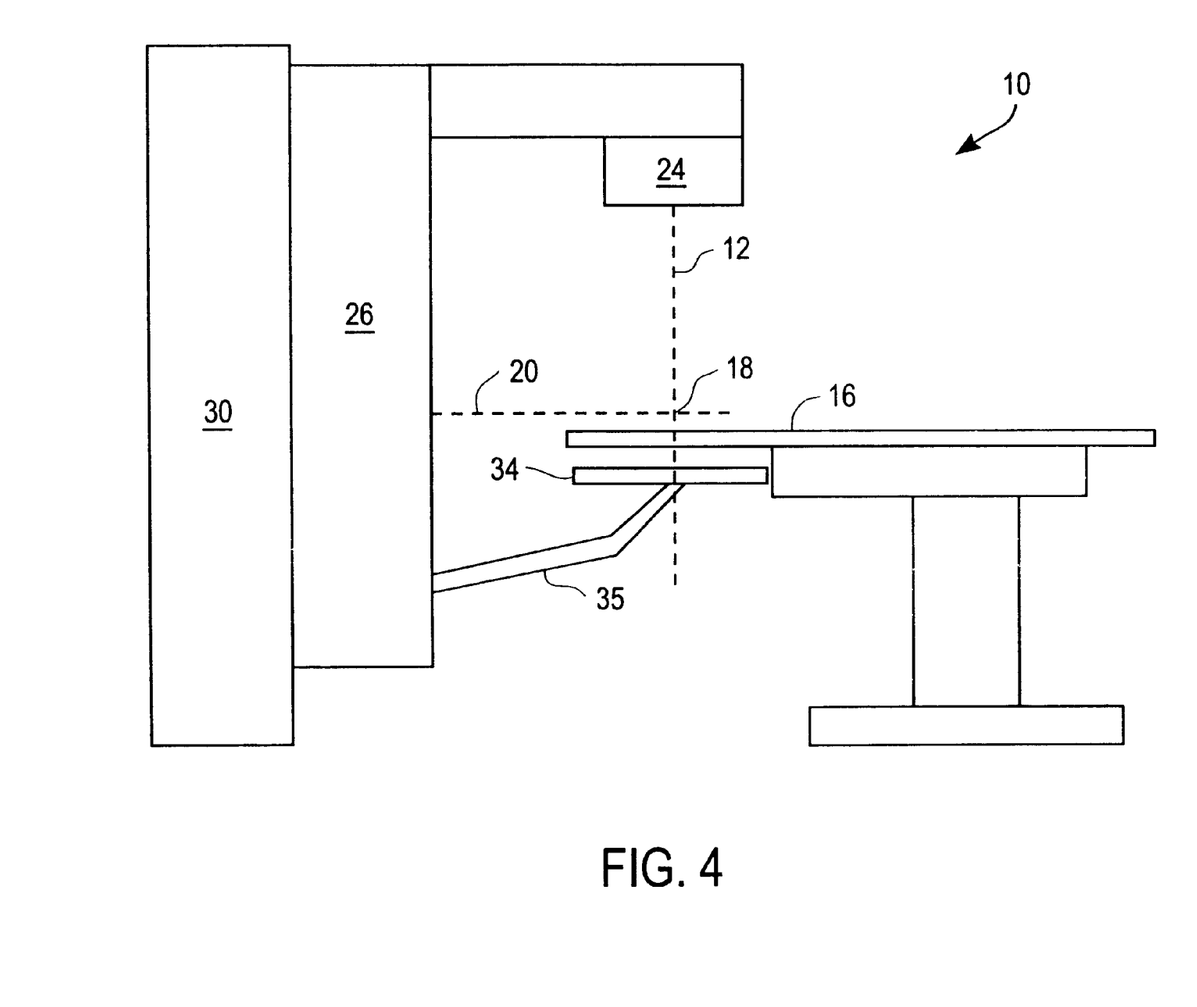
FIG. 4 is a side view of the radiation therapy device of FIG. 1 showing an extended portal imaging device.

Referring now to FIG. 4, a further side view of portions of radiation therapy device 10 is shown. In this view, imaging device 34 is extended in an imaging position along beam path 12. That is, in this position, imaging device 34 may be operated to capture one or more portal images. Positioning of imaging device 34 between the retracted and extended positions is performed under the control of computer 40 manipulating imaging device drive 47 via imaging device control 49 or gantry control 44 (FIG. 2). Further, in some embodiments, positioning of imaging device 34 is integrated with the overall operation of radiation therapy device 10 to delivery a prescribed course of treatment. As a result, portal images may be taken at various points during a treatment, allowing a radiation therapist to verify the field shape and patient position without need for the therapist to enter the treatment room or manually position or adjust the imaging device.

Figure 5:
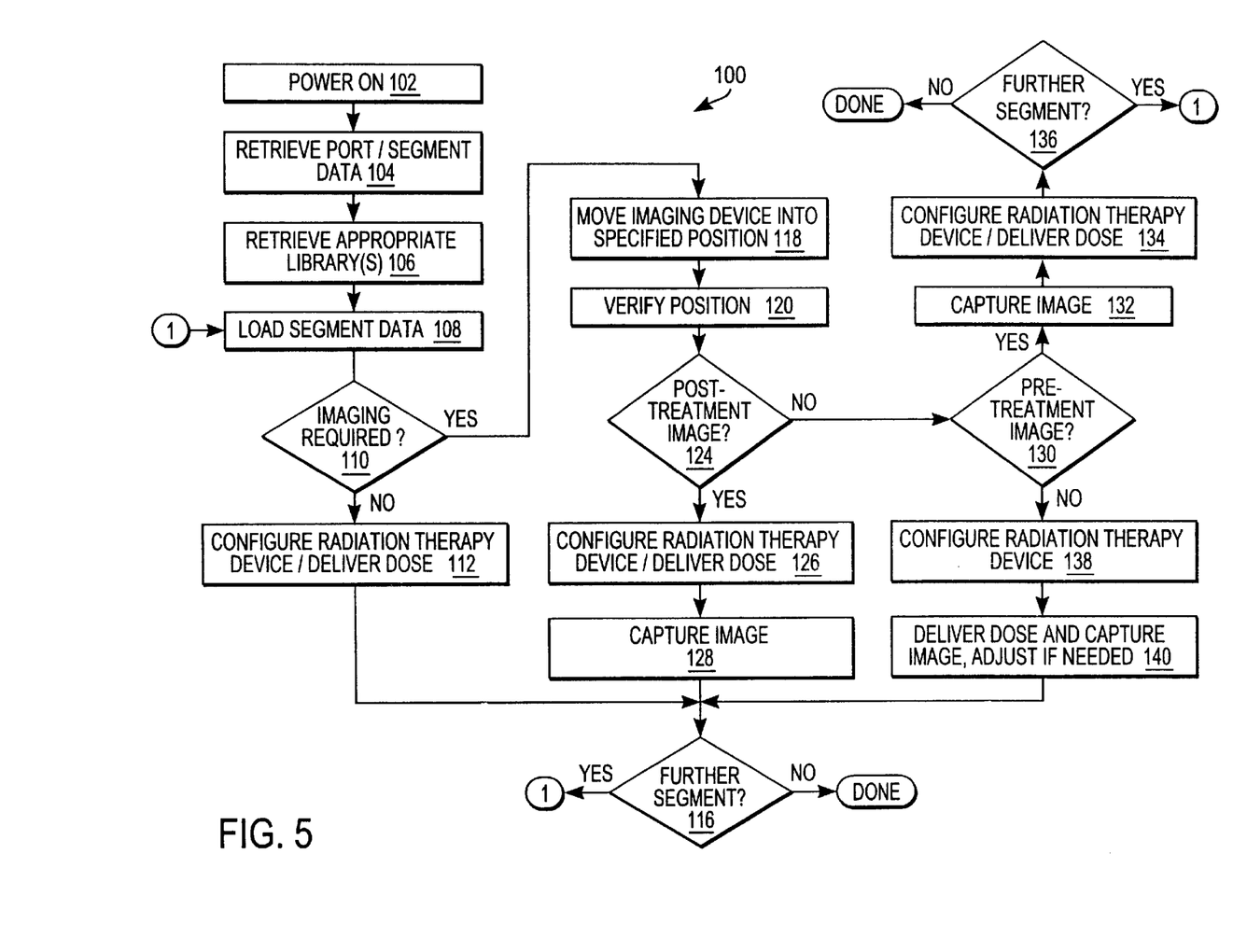
FIG. 5 is a flow diagram illustrating a process for the control of a portal imaging device of FIG. 1 according to some embodiments of the present invention.

Referring now to FIG. 5, a flow diagram is shown depicting one embodiment of an automated process 100 for capturing portal images during operation of a radiation therapy device. This processing may be performed under the control of computer program code stored at, or accessible by, computer 40 of treatment processing unit 32. The particular arrangement of elements in the flow chart of FIG. 5 is not meant to imply a fixed order to the steps; embodiments of the present invention can be practiced in any order that is practicable.

Processing begins at 102 where equipment, including radiation therapy device 10 and treatment processing unit 32, are powered on or otherwise enabled for use. Processing continues at 104 where port and segment data is retrieved. According to one embodiment, treatment processing unit 32 may store one or more courses of treatment prescribed for patients by oncologists. These courses of treatment may be stored as one or more treatment segments or groups associated with each patient. This information may be stored at, or accessible to, computer 40.

Processing at 104 may involve data entry by a radiation therapist operating operator console 42 to select a particular segment. In some embodiments, a particular segment is selected by computer 40 once patient information has been selected or entered. According to embodiments of the present invention, each segment may define a particular radiation therapy to be delivered (e.g., a defined shape and dose of primary electrons, primary photons, or a mixture of both), as well as one or more portal images to be captured within the segment.

Processing continues at 106 where appropriate libraries are retrieved or otherwise identified. Mass storage device 46 (or other devices in communication with computer 40) may store or have accessible to it, one or more interlock, or safety libraries which define permissible control sequences for each treatment type (e.g., different interlocks may be defined for primary photon fields that for primary electron fields) and for each port position. Other libraries and/or data files may also be retrieved at 106, including, for example configuration files defining one or more configurable features of components of radiation therapy device 10. In one embodiment, appropriate libraries and other data files are selected at 106 based on the particular segment retrieved at 104. These libraries will be used to configure and control components of radiation therapy device 10 during delivery of each field of the segment, including the positioning and operation of imaging device 34.

Processing continues at 108 where particular segment data from the data retrieved at 104 is loaded for processing. Each segment may include one or more individual instructions, each defining radiation fields to be delivered by radiation therapy device 10, as well as one or more imaging device positions to be adjusted for each field. Each instruction may be separately parsed by computer 40 and used to position components of radiation therapy device 10 to deliver the prescribed field and to capture a desired portal image. At 108, the instruction is loaded for processing.

Processing continues at 110 where a determination is made whether the segment data loaded at 108 requires the operating of imaging device 34 to perform imaging. Some fields or segments may not require any positioning of imaging device 34 (i.e., the imaging device may remain in the retracted position). Other fields may require the capture of one or more images requiring the positioning of imaging device 34 in the extended position.

If processing at 110 indicates that no image is to be taken, processing continues at 112 where the segment data loaded at 108 is used to configure radiation therapy device 10 and to operate radiation therapy device to deliver a prescribed dose of therapeutic radiation. Processing continues to 116 where a determination is made whether the therapy includes further segment data (e.g., defining further fields to be delivered). If further segment data is included in the therapy, processing reverts back to 108 where the next segment data is loaded for processing. If processing at 1 16 indicates that no further segments are included in the therapy, processing completes.

If processing at 110 indicates that imaging is required, processing continues to 118 where the segment data loaded at 108 is used to direct the positioning of imaging device 34. This positioning may be performed under the control of imaging device control 49 or gantry control 44 operating one or more imaging device drives 47 to position imaging device 34. For example, imaging device drive 47 may be operated to extend imaging device 34 to a position along beam path 12 (FIG. 4). At 120 (which may be an optional step) processing includes verifying that the imaging device is in the desired position. This verification may be performed by detecting control signals from imaging device drive 47 or from one or more sensors positioned to verify the position of imaging device 34.

Processing continues at 124 where a determination is made whether the image to be captured is a post-treatment image. If it is, processing continues at 126 where the segment data loaded at 108 is used to configure radiation therapy device 10 and to operate radiation therapy device to deliver a prescribed dose of therapeutic radiation. After delivery of the radiation, processing continues at 128 where a dose of radiation necessary for an image is generated while imaging device 34 is operated to capture a portal image. The portal image captured at 128 may be transmitted to computer 40 for processing. Processing continues to 116 where a determination is made whether the therapy includes further segment data (e.g., defining further fields to be delivered).

If processing at 124 indicated that the image to be taken is not a post-treatment image, processing continues to 130 where a determination is made whether the image to be captured is a pre-treatment image. If so, processing continues to 132 where a dose of radiation necessary for an image is generated while imaging device 34 is operated to capture a portal image. The portal image may be transmitted to computer 40 for manipulation and further processing. Processing continues at 134 where the segment data loaded at 108 is used to configure radiation therapy device 10 and to operate radiation therapy device to deliver a prescribed dose of therapeutic radiation. Processing continues to 136 where a determination is made whether the therapy includes further segment data (e.g., defining further fields to be delivered). If further segment data is provided, processing reverts to 108 where the next segment data is loaded and the process repeats. Otherwise, processing completes.

If processing at 130 indicated that the image to be taken is not a pre-treatment image, processing continues to 138 where the segment data loaded at 108 is used to configure radiation therapy device 10 to prepare for delivery of a therapeutic dose of radiation. Processing continues at 140 where segment data loaded at 108 is used to operate radiation therapy device 10 while simultaneously operating imaging device 34 to capture one or more portal images during delivery of the radiation. Again, the captured image(s) may be transmitted to computer 40 for further processing and analysis. Processing continues to 116 where a determination is made whether the therapy includes further segment data (e.g., defining further fields to be delivered). If further segment data is provided, processing reverts to 108 where the next segment data is loaded and the process repeats. Otherwise, processing completes.

Although the above process has been described as a single process which allows integrated control and use of imaging device 34 to take pre-post- and mid-treatment portal images, those skilled in the art will recognize that the processing of FIG. 5 may be broken into discrete subcomponents which are followed based on an overall treatment plan. Images captured by imaging device 34 may be manipulated and viewed by an operator or oncologist to adjust future treatments, adjust device settings, or take other corrective actions. In some embodiments, image processing techniques may be used by computer 40 to manipulate the images captured.

Those skilled in the art will appreciate that various adaptations and modifications of the just described preferred embodiments can be configured without departing from the scope and spirit of the invention. Therefore, it is to be understood that, within the scope of the appended claims, the invention may be practiced other than as specifically described herein.

What is claimed is:

1. A method for operating a radiation therapy device, comprising:
   identifying segment information defining a radiation therapy treatment segment;
   identifying, from said segment information, portal position information; and
   positioning a portal imaging device based on said portal position information.

2. The method of claim 1, further comprising:
   identifying, from said segment information, field information defining a radiation field to be delivered;
   positioning elements of said radiation therapy device to deliver said radiation field defined by said field information;
   delivering said radiation field; and
   capturing a portal image of said radiation field on said portal imaging device.

3. The method of claim 1, wherein said portal imaging device is a flat panel detector movably coupled to a gantry of said radiation therapy device.

4. The method of claim 1, wherein said positioning of said portal imaging device includes providing control signals from an operator console to a drive motor coupled to said portal imaging device.

5. The method of claim 2, wherein said portal imaging device comprises a plurality of solid state sensors.

6. The method of claim 2, further comprising:
   transmitting said portal image to a treatment unit.

7. The method of claim 1, further comprising:
   repeating said identifying segment information, identifying portal position information, and positioning said portal imaging device for each segment in a radiation therapy treatment.

8. The method of claim 2, further comprising:
   further positioning, based at least in part on said portal image, elements of said radiation therapy device.

9. A computer-operated method for capturing portal images in a radiation therapy device, comprising:
   retrieving first data identifying a first therapy segment;
   identifying, from said first data, position data defining a position for a portal imaging device;
   generating signal data causing a drive device to place said portal imaging device in said position; and
   verifying that said portal imaging device is in said position.

10. The computer-operated method of claim 9, further comprising:
    identifying, from said first data, field data defining a radiation field to be delivered by said radiation therapy device;
    generating signal data to position elements of said radiation therapy device to deliver said radiation field defined by said field data;
    generating signal data to cause said radiation therapy device to deliver said radiation field; and
    operating said portal imaging device to capture a portal image.

11. The computer-operated method of claim 10, wherein said radiation field is a diagnostic field and said portal image is a pre-treatment image captured before a dose of therapeutic radiation is delivered to a patient.

12. The computer-operated method of claim 10, wherein said radiation field is a diagnostic field and said portal image is a post-treatment image captured after a dose of therapeutic radiation has been delivered to a patient.

13. The computer-operated method of claim 10, wherein said portal image is captured during said delivery of said radiation field.

14. The method of claim 10, further comprising:
    forwarding said portal image to a treatment unit.

15. A radiation therapy device, comprising:
    a radiation source, configured to deliver a beam of radiation along a target path toward a treatment zone;
    a gantry, configured to rotate said radiation source about a first axis of rotation, said gantry further configured to rotate an imaging system about said first axis;
    a drive device, coupled to said imaging system, to selectively extend and retract said imaging system across said target path; and
    a control computer configured to position said drive device, said gantry and said radiation source based on data defining a radiation therapy treatment.

16. The radiation therapy device of claim 15, wherein said imaging system is a flat panel imaging device comprising a plurality of solid state sensors.

17. The radiation therapy device of claim 15, wherein said control computer is further configured to operate said imaging system to capture a portal image.

18. An imaging system used in conjunction with a radiation therapy device, comprising:
    a drive device, coupled to a computer system of said radiation therapy device,
    an imaging panel having a plurality of sensors adapted to detect radiation; and
    an arm assembly, attached to said imaging panel and to said drive device;
    wherein said drive device selectively positions said imaging panel in one of an extended or retracted position based on data received from said computer system.

19. A radiation therapy device, comprising:
    means for identifying segment data identifying a radiation therapy treatment segment;
    means for identifying, from said segment data, portal position data; and
    means for positioning a portal imaging device based on said portal position data.

20. A computer program product in a computer readable medium for operating a radiation therapy device, comprising:

first instructions for identifying segment data identifying a radiation therapy treatment segment;
second instructions for identifying, from said segment data, portal position data; and
third instructions for positioning a portal imaging device based on said portal position data.

* * * * *